(12) United States Patent
Ahrer et al.

(10) Patent No.: US 12,233,126 B2
(45) Date of Patent: *Feb. 25, 2025

(54) HIGH CONCENTRATION IMMUNOGLOBULIN COMPOSITION FOR PHARMACEUTICAL APPLICATION

(71) Applicant: OCTAPHARMA AG, Lachen (CH)

(72) Inventors: Karin Ahrer, Vienna (AT); Waltraud Kaar, Vienna (AT); Ulrich Roessl, Vienna (AT)

(73) Assignee: OCTAPHARMA AG, Lachen (CH)

( * ) Notice: Subject to any disclaimer, the term of this patent is extended or adjusted under 35 U.S.C. 154(b) by 419 days.

This patent is subject to a terminal disclaimer.

(21) Appl. No.: 17/519,141

(22) Filed: Nov. 4, 2021

(65) Prior Publication Data

US 2022/0233692 A1 Jul. 28, 2022

Related U.S. Application Data

(63) Continuation of application No. 16/308,356, filed as application No. PCT/EP2017/064279 on Jun. 12, 2017, now Pat. No. 11,191,833.

(30) Foreign Application Priority Data

Jun. 10, 2016 (EP) .................................... 16174019

(51) Int. Cl.
| | | |
|---|---|---|
| *A61K 39/395* | (2006.01) | |
| *A61K 9/00* | (2006.01) | |
| *A61K 9/08* | (2006.01) | |
| *A61K 47/18* | (2017.01) | |
| *A61K 47/22* | (2006.01) | |
| *A61K 39/00* | (2006.01) | |

(52) U.S. Cl.
CPC ...... *A61K 39/39591* (2013.01); *A61K 9/0019* (2013.01); *A61K 9/08* (2013.01); *A61K 47/183* (2013.01); *A61K 47/22* (2013.01); *A61K 2039/505* (2013.01)

(58) Field of Classification Search
None
See application file for complete search history.

(56) References Cited

U.S. PATENT DOCUMENTS

| 4,597,966 | A | 7/1986 | Zolton et al. |
|---|---|---|---|
| 8,613,919 | B1 | 12/2013 | Ma et al. |
| 11,191,833 | B2 * | 12/2021 | Ahrer ...................... A61K 9/08 |
| 2007/0122402 | A1 | 5/2007 | Bolli et al. |
| 2013/0121991 | A1 | 5/2013 | Huille et al. |

FOREIGN PATENT DOCUMENTS

WO WO-2013/063510 A1 5/2013

OTHER PUBLICATIONS

Bolli et al., L-Proline reduces IgG dimer content and enhances the stability of intravenous immunoglobulin (IVIG) solutions, Biologicals, 38(1):150-7 (Jan. 2010).
Chi et al., Physical stability of proteins in aqueous solution: mechanism and driving forces in nonnative protein aggregation, Pharm. Res., 20(9):1325-36 (Sep. 2003).
Falconer et al., Stabilization of a monoclonal antibody during purification and formulation by addition of basic amino acid excipients, J. Chem. Tech. & Biotech., 86(7):942-8 (Jul. 2011).
International Application No. PCT/EP2017/064279, International Search Report and Written Opinion mailed Sep. 11, 2017.
Mccue et al., Three generations of immunoglobulin G preparations for clinical use, Rev. Infect. Dis., 8 Suppl. 4:S374-81 (Jul.-Aug. 1986).
Mueller et al., Liquid formulations for long-term storage of monoclonal IgGs, Appl. Biochem. Biotechnol., 169(4):1431-48 (Feb. 2013).
Szenczi et al., The effect of solvent environment on the conformation and stability of human polyclonal lgG in solution, Biologicals, 34(1):5-14 (Mar. 2006).
Trevino et al., Measuring and increasing protein solubility, J. Pharm. Sci., 97(10):4155-66 (Oct. 2008).
Vermeer et al., The thermal stability of immunoglobulin: unfolding and aggregation of a multi-domain protein, Biophys. J., 78(1):394-404 (Jan. 2000).
Wang et al., Antibody structure, instability, and formulation, J. Pharm. Sci., 96(1):1-26 (Jan. 2007).
Weiss et al., Principles, approaches, and challenges for predicting protein aggregation rates and shelf life, J. Pharm. Sci., 98(4):1246-77 (Apr. 2009).

\* cited by examiner

*Primary Examiner* — Yunsoo Kim
(74) *Attorney, Agent, or Firm* — MARSHALL, GERSTEIN & BORUN LLP (57) ABSTRACT

The present invention relates to a liquid composition comprising polyclonal immunoglobulins, at least one viscosity modulating amino acid, selected from arginine and histidine, and at least one stabilising amino acid, selected from glycine and proline, wherein more than 90% of the polyclonal immunoglobulins are in the form of monomers or dimers and less than 5% in the form of polymers, and wherein the immunoglobulin concentration in the composition is above 160 g/L and the pH is in the range from 5.2 to 5.9. The invention further relates to a liquid composition for use in medical treatment, to amino acids for formulating a highly concentrated polyclonal immunoglobulins as well as a method of formulating.

16 Claims, 3 Drawing Sheets

HIGH CONCENTRATION IMMUNOGLOBULIN COMPOSITION FOR PHARMACEUTICAL APPLICATION

CROSS-REFERENCE TO RELATED APPLICATIONS

This Application is a Continuation of U.S. patent application Ser. No. 16/308,356, filed on Dec. 7, 2018 (§ 371 (c) date), which is a U.S. National Phase of International Patent Application No. PCT/EP2017/064279, filed on Jun. 12, 2017, which claims priority under § 119 to European Patent Application No. 16174019.6, filed on Jun. 10, 2016.

TECHNICAL FIELD OF THE INVENTION

The present invention relates to a liquid composition comprising a high concentration of immunoglobulins with improved handling, administration and storage properties.

BACKGROUND OF THE INVENTION

Immunoglobulins or antibodies are used by the immune system to identify and neutralize pathogens like viruses and bacteria. Accordingly, human immunoglobulin concentrates have been used for a long time for the treatment and prevention of diseases such as infectious diseases and immunodeficiencies.

Immunoglobulin preparations are generally administered intravenously (i.v.), subcutaneously (s.c.) or intramuscularly (i.m.). If the administration is via the s.c. or i.m. route, immunoglobulin preparations should have a low volume and therefore a high immunoglobulin concentration for the patients convenience as large volumes applied into subcutaneous or muscle tissue can lead to irritation and pain and can prolong application time.

However, an increase in protein concentration has an influence on protein stability, aggregation and viscosity of the composition. Besides conformational stability aspects, association and aggregation plays an important obstacle in high protein concentrations since a higher rate of molecular collisions is expected to increase intermolecular protein association and subsequent aggregation.

Moreover, immunoglobulin preparations generally experience an exponential rise of viscosity during increase of immunoglobulin concentration, in particular due to the tendency to protein aggregation.

An increase of formulation viscosity limits the syringeability and applicability for subcutaneous administration via thin syringe needles. Additionally, high viscosity can impose problems during processing, such as during diafiltration or filling. It is consequently desirable to keep the viscosity of drugs to be infused or injected as low as possible It is also desirable to provide conformationally stable immunoglobulin preparations which have long storage stability. In general, conformational stability of immunoglobulins is high near the isoelectric point (pI) (Mueller et al. 2013).

Solubility of proteins is however minimal at the pI (Wang et al., 2008), which can become an issue particularly for IgG preparations of higher concentration.

McCue and co-workers demonstrated that pIs in human plasma IgG range between pH 4.5 and 11, exhibiting a clear maximum between pH 7 and pH 9. The group also found an increase of oligomeric species and disturbance of binding properties at neutral pH and above (McCue et al. 1986).

On the other hand, under acidic conditions conformational stability drops due to higher protein surface charge (Chi et al., 2003). Notably, pH values below 4 in particular can lead to fragmentation and aggregation of IgG (Bolli et al., 2010; Wang et al., 2007; Vermeer et al., 2000 or Szenczi et al., 2006).

One way to reduce the viscosity of such immunoglobulin concentrates is by altering the pH of the concentrates to high or low values. WO 02/30463 A2, for example, describes a method of lowering the viscosity of a concentrated immunoglobulin composition with a concentration of at least 80 g/L by altering the pH of the formulation to lower (4.0 to 5.3) or elevated values (6.5 to 12.0), buffers or salts are added in a concentration of 50 to 200 mM. As an alternative the document suggests increasing the total ionic strength of the formulation through the addition of salts or buffer components.

Figure 1:
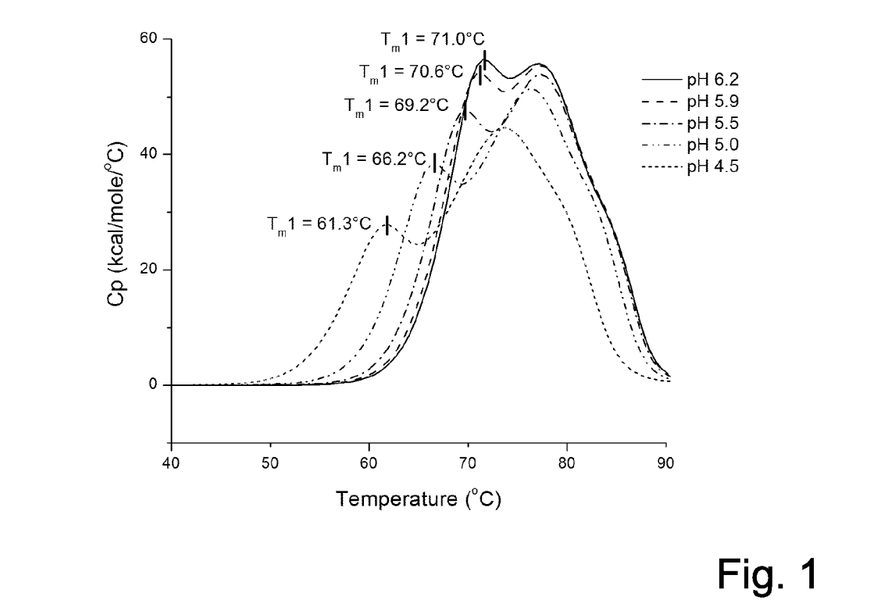
FIG. 1 shows thermal transition curves of compositions comprising human plasma-derived IgG. The thermal transition curves represent the molar heat capacity of the composition in dependence of the temperature and are determined by DSC measurements. The compositions comprise IgG, 20 mM NaCl, 20 mM sodium acetate and differ in pH as indicated in the figure (pH 4.5, 5.0, 5.5, 5.9, 6.2). The local maxima of the curves represent unfolding transitions. The exact temperatures of the first maximum ($T_m1$) are identified for each curve. The $T_m1$-temperatures for said IgG solutions at various pH values were 61.3° C. for pH=4.5, 66.2° C. for pH=5.0, 69.2° C. for pH=5.5, 70.6 for pH=5.9 and 71.0° C. at pH=6.2.

Reduction of the pH leads to a decrease in protein stability and tendency to unfolding as shown in Example 1 and FIG. 1. During long term storage the consequence is increased protein fragmentation. On the other hand an increase of the pH to values in the range from 6.5 to 9 decreases the solubility of immunoglobulins, while pH values above 10 induce conformational instability during long term storage.

For other pharmaceutical formulations, namely formulations comprising monoclonal antibodies WO 2013/063510 A1 describes the use of amino acids for viscosity reduction. However, it is not known whether these findings are applicable to highly concentrated human plasma derived immunoglobulins and—if so—which of the myriad of amino acids and amino acid combinations would have a viscosity reducing effect.

Thus, it is an object of the invention to provide formulations for stabilizing human plasma derived immunoglobulins at high concentrations.

SUMMARY OF THE INVENTION

The present invention is, inter alia, based on the finding that formulating highly concentrated immunoglobulin compositions with combination of a certain slightly acidic pH range, in particular from pH 5.5 to 5.9 and the addition of a stabilizing amino acid, such glycine or proline, as well as viscosity reducing amino acid, such as histidine or arginine, in certain amino acid concentrations leads to compositions that both are of reduced viscosity and increased stability.

Accordingly, the present invention provides a liquid composition comprising polyclonal immunoglobulins, at least one viscosity modulating amino acid, selected from arginine and histidine, and at least one stabilising amino acid, selected from glycine and proline, wherein more than 90% of the polyclonal immunoglobulins are in the form of monomers or dimers and less than 5% in the form of polymers, and wherein the immunoglobulin concentration in the composition is above 160 g/L and the pH is in the range from 5.5 to 5.9.

This combination leads to a highly concentrated immunoglobulin composition which is low enough in viscosity to allow good processing of the composition as well as sufficient syringeability. Moreover, the immunoglobulins in the compositions are stable enough for long term storage. This means that the generation of immunoglobulin fragments is minimized and the immunoglobulins have a low a tendency to form polymers.

In a second aspect, the invention relates to a liquid composition according to the first aspect for use in medical treatment.

According to a third aspect, the invention relates to the method of formulating a highly concentrated polyclonal immunoglobulin composition, comprising the steps of providing a highly concentrated polyclonal immunoglobulin composition, adjusting the pH of the composition to a value in the range from 5.5 to 5.9, and adding at least one stabilizing amino acid, selected from glycine and proline, and at least one viscosity modulating amino acid, selected from arginine and histidine.

DETAILED DESCRIPTION

According to a first aspect, the present invention provides a liquid composition comprising polyclonal immunoglobulins, at least one viscosity modulating amino acid, selected from arginine and histidine, and at least one stabilising amino acid, selected from glycine and proline, wherein more than 90% of the polyclonal immunoglobulins are in the form of monomers or dimers and less than 5% in the form of polymers, and wherein the immunoglobulin concentration in the composition is above 160 g/L and the pH is in the range from 5.5 to 5.9.

The polyclonal immunoglobulins according to the present invention are derived from human plasma. The polyclonal immunoglobulins according to the invention may comprise immunoglobulin G (IgG), immunoglobulin A (IgA), immunoglobulin M (IgM). The polyclonal immunoglobulins are in particular a human IgG concentrate. An IgG concentrate then generally comprises different impurities such as other immunoglobulins like IgA or IgM and further blood proteins such as albumin.

The main component of the immunoglobulin preparations are the immunoglobulins. Thus, in the composition according to the invention the content of immunoglobulins is more than 90%, preferably more than 95% and more preferably more than 98% based on total protein.

The total protein as used herein refers to the total protein concentration determined with the Biuret-Assay, which is based on the development of a violet colour when copper-(II)-ions react with amino groups at alkaline pH.

An Immunoglobulin G (IgG) concentrate according to the invention may for example be prepared as described in WO 2005/082937 A2. Accordingly, the starting material was Fraction I+II+III prepared from a plasma pool according to cold ethanol fraction technology (such as Cohn, Kistler-Nitschmann or modifications thereof).

Reconstituted Fraction I+II+III can then be processed using caprylate precipitation and anion-exchange chromatographies. Dedicated pathogen safety steps comprised solvent/detergent (S/D) treatment, subsequent S/D reagent removal as well as nanofiltration.

For product improvement methods targeting further impurity load reduction additional measures might be incorporated, for instance for reduction of haemagglutinins by contact with affinity resins based on certain trisaccharides like disclosed in WO-A2-01/27623. These immunoglobulin preparation methods usually include at least a solvent/detergent (S/D) treatment and a nanofiltration step for pathogen safety reasons.

As used herein, the term "immunoglobulin" refers to proteins that bind to specific antigens. Immunoglobulins include but are not limited to, polyclonal, monoclonal, chimeric and humanized antibodies, and include the following classes: IgA, IgG, IgM, IgD, and IgE. Immunoglobulins generally comprise two identical heavy chains and light chains. However the term immunoglobulin as used herein also includes fragments such as the single chain immunoglobulins, as well as protein dimers, polymers or aggregates.

The polyclonal immunoglobulins in the liquid composition according to the invention show a low level of polymerization, confirmed by molecular size distribution measurement. This means the polyclonal immunoglobulins comprise at least 90% monomers and dimers as a sum and at most 5% polymers. Moreover, the polyclonal immunoglobulins show only low degree of fragmentation. This means that at most 5% of the polyclonal immunoglobulins are fragments. The percentages are calculated from the area under the curve for aggregates, dimers, monomers and fragments measured by size exclusion high pressure liquid chromatography. It should be noted that it is not strictly differentiated within this document between aggregates and polymers or between aggregation and polymerisation as the skilled person is aware that molecules or molecule clusters, respectively their formation process, of higher molecular weight than the weight of immunoglobulin dimers are meant. As a consequence the total sum of monomers, dimers, polymers and fragments of immunoglobulins is 100%. The percentage of polymers of at most 5% is significantly below the threshold required according to pharmacopeia.

In a preferred embodiment of the invention the polyclonal immunoglobulins comprise at least 94% monomers and dimers as a sum, at most 5% polymers and at most 5% fragments. This means, as the percentages are always based on the total sum of monomers, dimers, polymers and fragments, that the sum of polymers and fragments is less than 6%.

The molecular size distribution as used herein is measured by size exclusion high pressure liquid chromatography (SE-HPLC or SEC) with a hydrophilic silica gel suitable for fractionation of globular proteins with relative molecular masses of 10000 to 500000 and detection with a spectrophotometer at 280 nm. The result is reported as % of area under the curve for aggregates, dimers, monomers and fragments.

The immunoglobulin concentration, in the liquid composition according to the invention is above 160 g/L. immunoglobulin concentrations below this value are not considered as a highly concentrated immunoglobulin composition. Lower concentrated immunoglobulin compositions do not experience the viscosity problems as highly concentrated immunoglobulin compositions do.

According to the invention, if not stated otherwise, the immunoglobulin concentration is determined by SEC. The immunoglobulin is determined by SEC with the same equipment used for molecular size distribution. In order to obtain quantitative results it is necessary to compare the obtained area under the curve of an immunoglobulin sample with values obtained by establishment of a calibration curve with a calibration material of know immunoglobulin concentration. For sufficiently pure immunoglobulin compositions additional corrections of the obtained value are not necessary.

The pH of the liquid composition is in the range from 5.5 to 5.9. As outlined in the introduction IgG solubility and with that the propensity of IgG to form polymers and aggregates increases when approaching neutral pH values. However, as shown in the example presented in FIG. 2 the percentage of polymers is still acceptable. Higher pH values are not recommended as this might lead to significantly higher aggregation. Thus, the maximum pH according to the invention is 5.9.

In addition, there is a lower limit for the pH of the liquid immunoglobulin composition. As is shown in example 1 the thermodynamic stabilities of the immunoglobulins in the compositions are significantly decreased at pH values of 4.5 and 5.0 as compared to the higher pH values of 5.5 to 6.2. From this it is assumed that a pH value of 5.2 might be acceptable with respect to protein stability and fragmentation. However, with a pH range between pH 5.5 and pH 5.9 it is possible to retain thermodynamically stable conditions without approaching the maximum of the pI distribution.

As used herein, if not stated otherwise the viscosity of the composition is the dynamic viscosity. According to the invention the dynamic viscosity is determined with the Automated Microviscositymeter "AMVn" from Anton Paar® GmbH (Austria) at a temperature of +20.0° C. and a capillary inclination angle of 50°. The determination is performed according to the instruments instruction manual. The result of the measurement is the kinematic viscosity. In order to obtain the dynamic viscosity, in addition the density is determined with the "DMA 4500M" densitometer also from Anton Paar® GmbH (Austria) at the same temperature. The product of the kinematic viscosity and the density is the dynamic viscosity.

Differential Scanning calorimetry (DSC) is used in order to assess protein stability towards thermal denaturation. In relation to a calorimetric reference the enthalpy change upon protein thermal unfolding and the thermal unfolding midpoint ($T_m$) of single or multiple transitions is measured. DSC is considered a reasonable technique for the predictive estimation of protein aggregation over a certain desired time (shelf life), especially in cases when a ranking of (formulation) conditions in terms of conformational stability is desired (Mueller et al. 2013 and Weiss et al. 2009).

During prolonged storage aggregation, polymerisation and fragmentation and a corresponding reduction of the sum of the monomer and dimer fraction of the immunoglobulin may occur.

It should be noted that it is not strictly differentiated within this document between aggregates and polymers or between aggregation and polymerisation as the skilled person is aware that molecules or molecule clusters, respectively their formation process, of higher molecular weight than the weight of immunoglobulin dimers are meant.

"Storage stability" for the defined time span as used herein means that the immunoglobulins in the composition have a molecular size distribution of more than 90% monomers and dimers as a sum, at most 5% polymers and at most 5% fragments and wherein the total sum of monomers, dimers, polymers and fragments is 100% after storage for the defined time span. For example, if it is defined that the immunoglobulin composition has a storage stability for sixty months it means that for at least 60 months the molecular size distribution shows more than 90% monomers and dimers as a sum, at most 5% polymers and at most 5% fragments.

The liquid composition according to the invention comprises two types of amino acids. The first type is the viscosity modulating amino acid, selected from arginine and histidine. As shown in example 4, the addition of either one of arginine and histidine to an immunoglobulin composition leads to a significant reduction of viscosity of the composition with high concentration of immunoglobulin. With these two viscosity modulating amino acids it is possible to adjust the viscosity of the formulation to values that are preferable for administering the composition via a syringe.

The second type of amino acid in the liquid composition according to the invention is the stabilizing amino acid. The stabilizing amino is selected from glycine and proline. As shown in example 3, both the addition of glycine or proline leads to a significant increase in thermal stability.

Moreover, as shown in examples 5 and 6 the combination of the viscosity modulating amino acid and the stabilizing amino acid has both effects. From example 5 it even appears that the combination of stabilizing and viscosity modulating amino acids leads to the same stabilization as the stabilizing amino acid only. Also, the stabilizing amino acid has no negative impact on the viscosity of the composition when added to the viscosity modulating amino acid.

According to one embodiment the immunoglobulin concentration of the liquid composition is in the range from 150 to 300 g/L, preferably in the immunoglobulin concentration is in the range from 160 to 260 g/L. When the immunoglobulin concentration exceeds 300 g/L it is not possible anymore with the components according to the present invention to decrease the viscosity to the range in which the liquid composition can be handled or administered by a syringe. As shown in the examples, up to a concentration of 260 g/L formulations can be obtained with a reasonable viscosity and long-term storage stability.

Figure 2:
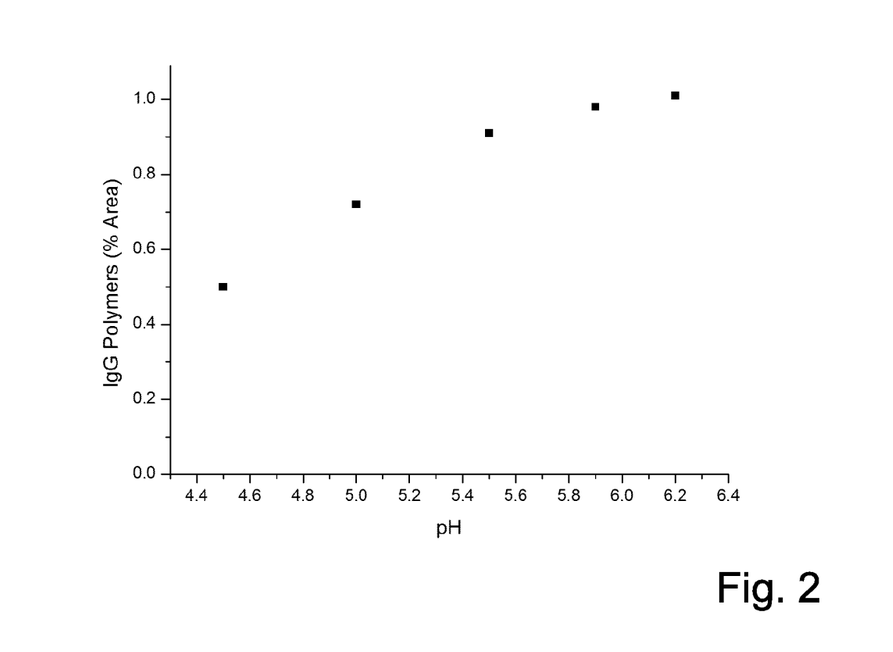
FIG. 2 shows qualitatively the relation between the pH of an IgG preparation and the fraction of IgG polymers. The IgG polymer fraction of the IgG composition (20 mM NaCl, 20 mM sodium acetate) is measured by SEC and defined in % based on the total IgG at various pH values.

The pH of the liquid composition is in the range from 5.5 to 5.9. The pH value of 5.9 has a sufficient distance from the isoelectric point of the immunoglobulins, in particular IgG. Accordingly, the value of 5.9 leads to lower formation of polymers or aggregates as compared to the value of 6.2. Thus keeping the pH below 5.9 is likely to lead to more stable and less aggregated formulations. As is shown in FIG. 2 the terminal instability increases strongly when decreasing the pH from 5.5 to 5.0. Thus, even if the pH of 5.2 might be suitable for the liquid composition according to the invention, a minimum of pH 5.5 provides a higher stability of the immunoglobulins in the liquid composition. Very good results with respect to viscosity and stability were obtained with a pH of 5.7. Thus according to one embodiment the pH is in the range from 5.6 to 5.8, in particular the pH is about 5.7.

According to one embodiment the liquid composition is characterized by a protein concentration in the range from 160 to 180 g/L dynamic viscosity in the range from 5 to 12 mPa*s. According to an alternative embodiment the liquid composition is characterized by a protein concentration in the range from above 180 to 220 g/L and a dynamic viscosity of >12 to ≤35 mPa*s. According to a further alternative embodiment the liquid composition is characterized by a protein concentration in the range from above 220 to 260 g/L and a dynamic viscosity of >35 to ≤100 mPa*s.

According to one embodiment of the present invention the concentration of the one or more stabilizing amino acid and the one or more viscosity modulating amino acid, i.e. the total concentration of the stabilizing amino acid(s) and a viscosity modulating amino acid(s) is in the range from hundred to 400 mM. Below a total concentration of 100 mM the concentration of the individual viscosity modulating and stabilizing amino acids will not be sufficient to provide a highly concentrated immunoglobulin composition with suitable viscosity and long term stability.

According to a preferred embodiment the total concentration of stabilizing and viscosity reducing amino acids is in the range from 150 to 350 mM. As shown in the examples, in particular example 7 total amino acid concentration within this range led to long term storage stability of the immunoglobulin compositions.

Particularly good results were obtained with a total concentration of stabilizing and viscosity modulating amino acids of about a 250 mM. Therefore, according to a preferred embodiment the total amino acid concentration of stabilizing and viscosity modulating amino acids is in the range from 200 to 300 mM, more preferably in the range from 225 to 275 mM, most preferably about 250 mM.

According to one embodiment the stabilizing amino acid is glycine and the viscosity modulating amino acid is arginine or a histidine. According to an alternative embodiment the stabilizing amino acid is proline and the viscosity modulating amino acid is arginine or histidine. According to a further alternative embodiment the stabilizing amino acid is glycine or proline and the viscosity modulating amino acids are arginine and histidine according to a further alternative embodiment the stabilizing amino acids are glycine and proline and the viscosity modulating amino acid is arginine or histidine. According to a further embodiment the stabilizing amino acids are glycine and proline and the viscosity modulating amino acids are arginine and histidine. According to a preferred embodiment the stabilizing amino acid is glycine and the viscosity modulating amino acid is arginine.

According to one embodiment the concentration of viscosity modulating amino acid in the liquid composition is in the range from 50 to 100 mM. Below 50 mM the viscosity reducing effect of the viscosity modulating amino acids is generally not sufficient to render the viscosity of the composition to a suitable value.

Above a value of 100 mM the destabilizing effect of the viscosity modulating amino acids becomes too strong so that extremely high concentrations of a stabilizing amino acid would be in it to counter the destabilizing effect and, consequently, the total concentration of amino acid would exceed 400 mM.

Preferably, the concentration of the viscosity modulating amino acid(s) is in the range from 60 to 90 mM. As shown in the examples in particular for arginine a concentration of 75 mM was found to provide the best results with respect to viscosity decrease and stabilization. Thus, preferably the concentration of the viscosity modulating amino acids is in the range from 65 to 85 mM, most preferably in the range from 70 to 80 mM and in particular about 75 mM. According to a preferred embodiment of the liquid composition contains arginine in the concentration of 70 to 80 mM.

According to one embodiment the concentration of the stabilizing amino acid is in the range from 80 to 300 mM. Below the concentration of 80 mM, it is assumed that the stabilizing affect cannot counteract the destabilizing effect of the viscosity modulating amino acids. Above the concentration of 300 mM total concentration of amino acids reaches into a range where the amino acids might interfere with the function of the immunoglobulins.

The preferred concentration in particular for the stabilizing amino acid glycine was found to be 175 mM, see example 7. Thus, according to a preferred embodiment, the concentration of the stabilizing amino acids is in the range from 130 to 220 mM. According to a more preferred embodiment the concentration is in the range from 160 to 190 mM. The more preferred concentration of the stabilizing amino acid is in the range from 170 to 180 mM. In particular the concentration is about 175 mM. According to a preferred embodiment the liquid composition contains the stabilizing amino acids in the concentration from 170 to 180 mM.

As shown in example 7, the immunoglobulins in the liquid composition according to the invention exhibit storage stability over a long period of time both at low temperatures in the range from 2 to 8° C. or at room temperature, which is in the range from 15 to 27° C.

According to one embodiment, the storage stability of the immunoglobulins in the liquid compositions is at least 40 months at a temperature of 2 to 8° C. Preferably, the term of storage stability is at least 60 months more preferably at least 69 month at the temperature of 2 to 8° C. At a storage temperature of 23 to 27° C., the term of storage stability of the immunoglobulins in the liquid composition according to the invention is at least 12 months storage, more preferably at least 24 months storage and most preferably at least 40 months storage.

Further excipients or stabilisers may also be present in the immunoglobulin preparation of the invention, but are not necessary for obtaining claimed stability. According to one embodiment the liquid composition may contain one or more of surfactant, detergent or saccharide. The liquid composition may also contain one or more of each of surfactant, detergent or saccharide. Examples of suitable saccharides are maltose, sorbitol, mannose, melezitose or glucose. An example of a suitable surfactant is polysorbate. Polysorbate is preferably present in the range from 5 to 60 mg/L.

According to one embodiment the liquid composition contains additionally a salt selected from sodium acetate, sodium chloride or sodium dihydrogen citrate. Preferably, the liquid composition comprises sodium acetate and NaCl. Sodium acetate is preferably present in the concentration of 10 to 50 mM. More preferably, sodium acetate is present in a concentration of about 20 mM. NaCl is preferably present in the concentration of 10 to 50 mM. More preferably, NaCl is present in a concentration of about 20 mM. According to one embodiment both sodium acetate and NaCl are present in a concentration of about 20 mM.

According to one embodiment of the present invention the liquid composition is virtually free of thrombogenic factors and have less than 2 mIU/ml FXIa-like activity referring to a 5% total protein solution being determined by the Thrombin Generation Assay (TGA) of Technoclone (Austria) using the NIBSC FXIa reference standard.

According to one embodiment the liquid composition of the present invention has haemagglutinins titers reduced to 16 for anti-A and 8 for anti-B when being determined by the Direct Coombs Test.

According to the invention the Direct Coombs Test is carried out according to the protocol defined in the Pharmacopoeia Europaea, In short, Anti-A or anti-B antibodies are contacted within this assay with papain and the titer, which is the highest dilution with agglutination being observed, is determined.

Preferred embodiments of the present invention are immunoglobulin G preparations with an immunoglobulin G content of 185-215 g/L, a pH value of 5.5-5.9 or 5.6-5.9 and a dynamic viscosity of >12 and up to 30 mPa*s, when being formulated with 150-210 mM glycine and 50-105 mM arginine. These preferred embodiments have a storage stability of at least 12 months at 23-27° C. and a storage stability of at least 24 months when being stored refrigerated at 2-8° C., with the stability of refrigerated immunoglobulin G preparations having been also determined after 67 and 69 months and were still found to be stable according to above defined criteria.

The immunoglobulin according to the invention can be used in the treatment or prevention of a variety of diseases. Thus, according to a second aspect, the present invention relates to a liquid composition comprising a high concentration of polyclonal immunoglobulins for use in medical treatment. Medical treatment according to the invention includes prevention and therapy.

In other words, according to a second aspect the present invention relates to treatment or prevention of diseases by administering the liquid composition comprising a high concentration of polyclonal immunoglobulins to the patient.

The liquid composition for use according to the second aspect comprises at least one stabilizing amino acid and at least one viscosity modulating amino acid. Further, the liquid composition according to the second aspect in particular has a pH in the range from 5.5 to 5.9. In particular the liquid composition according to the second aspect is in particular a liquid composition defined according to the first aspect.

The medical treatment includes the treatment and prevention of diseases such as immunodeficiency, like congenital agammaglobulinaemia, hypogammaglobulinaemia, common variable immunodeficiency, severe combined immunodeficiency, IgG subclass deficiencies with recurrent infections, myeloma, chronic lymphatic leukaemia with severe secondary hypogammaglobulinaemia, Alzheimer's disease, mild cognitive impairment (MCI), acquired auto immune deficiency syndrome (AIDS), Wiskott-Aldrich syndrome and severe combined immunodeficiency (SCID), acute and chronic idiopathic thrombocytopenic purpura (ITP), allogenic bone marrow transplantation (BMT), Kawasaki's disease, Guillan-Barre's syndrome, chronic inflammatory demyelinating polyneuropathy (CIDP), multifocal motoric neuropathy, Multiple Sclerosis, Myasthenia Gravis, Eaton-Lambert's syndrome, Rheumatoid arthritis, systemic lupus erythematosus, systemic scleroderma, vasculitis, Wegner's granulomatosis, Sjögren's syndrome, Autoimmune neutropenia, autoimmune haemolytic anaemia, neutropenia, Crohn's disease, colitic ulcerous, coeliac disease, asthma, septic shock syndrome, chronic fatigue syndrome, psoriasis, toxic shock or recurrent infections.

The treatment or prevention preferably comprises administering to a patient an effective amount of the liquid composition. The liquid composition can for example be administered in the form of a pharmaceutical composition.

Pharmaceutical compositions of the embodiments can be prepared and administered to a subject by any methods well known in the art of pharmacy. See, e.g, Goodman & Gilman's The Pharmacological Basis of Therapeutics, Hardman et al., eds., McGraw-Hill Professional (10th ed., 2001); Remington: The Science and Practice of Pharmacy, Gennaro, ed., Lippincott Williams & Wilkins (20th ed., 2003); and Pharmaceutical Dosage Forms and Drug Delivery Systems, Ansel et al. (eds), Lippincott Williams & Wilkins (7th ed., 1999). In addition, the pharmaceutical compositions of the embodiments may also be formulated to include other medically useful drugs or biological agents.

Pharmaceutical compositions according to the invention comprise the liquid composition with an effective amount of immunoglobulins, with the liquid composition additionally being formulated with at least one pharmaceutically acceptable carrier.

The pharmaceutically acceptable carrier is any carrier known or established in the art. Exemplary pharmaceutically acceptable carriers include sterile pyrogen-free water and sterile pyrogen-free saline solution.

Other forms of pharmaceutically acceptable carriers that can be utilized for the present embodiments include binders, disintegrants, surfactants, absorption accelerators, moisture retention agents, absorbers, lubricants, fillers, extenders, moisture imparting agents, preservatives, stabilizers, emulsifiers, solubilising agents, salts which control osmotic pressure, diluting agents such as buffers and excipients usually used depending on the use form of the formulation. These are optionally selected and used depending on the unit dosage of the resulting formulation.

The liquid composition or pharmaceutical composition may be administered to a patient by any customary administration route, e. g., orally, parenterally or by inhalation. Parenteral administration includes subcutaneous injection, intraperitoneal injection, intramuscular injection and intraperitoneal injection, liquid agents, suspensions, emulsions and dripping agents. Intramuscular (i.m.) and subcutaneous (s.c.) application is preferred.

According to a third aspect, the present invention relates to a method of formulating a highly concentrated polyclonal immunoglobulin preparation, comprising providing a highly concentrated polyclonal immunoglobulin preparation, adjusting the pH of the composition to a value in the range from 5.5 to 5.9, adding at least one stabilizing amino acid selected from glycine and proline and adding at least one viscosity modulating amino acid selected from arginine and histidine.

The product of this formulating method is a liquid composition comprising polyclonal immunoglobulins at least one stabilizing amino acid and one viscosity modulating amino acid with a pH in the range from 5.5 to 5.9. An immunoglobulin preparation is in particular an IgG concentrate which can be obtained as defined above.

According to one embodiment of the method the pH is adjusted to a value in the range from 5.5 to 5.9, more preferably in the range from 5.7 to 5.9, in particular to a pH of about 5.8.

In one embodiment of the method buffer components such as sodium acetate or NaCl are added to the immunoglobulin preparation before adding the amino acids and adjusting the pH.

According to one embodiment of the method the stabilizing amino acid is added to the highly concentrated polyclonal immunoglobulin composition before adding in the viscosity modulating amino acid and adjusting the pH. Accordingly, in a further step the viscosity modulating amino acid can be added before adjusting the pH.

Alternatively, as a next step the pH is adjusted to before adding the viscosity modulating amino acid.

In an alternative embodiment of the method the pH is adjusted before adding the stabilizing amino acid and viscosity modulating amino acid. Accordingly, in a next step the stabilizing amino acid is added. Alternatively the viscosity modulating amino acid is added before addition of the stabilizing amino acid.

A further alternative embodiment of the method comprises adding the viscosity modulating amino acid before adding the stabilizing amino acid and adjusting the pH. In this regard, in a next step the stabilizing amino acid can be added before adjusting the pH. Alternatively, the pH is adjusted before adding the stabilizing amino acid.

According to one embodiment the stabilizing and viscosity modulating amino acid are mixed before adding the mixture to the highly concentrated polyclonal immunoglobulin composition. This amino acid mixture can be added for adjusting the pH or alternatively after adjusting the pH.

In one embodiment of the method the immunoglobulin concentration of the resulting liquid composition is more than 160 g/L. Preferably, it is in the range from 160 to 300 g/L, more preferably in the immunoglobulin concentration is in the range from 160 to 260 g/L.

According to a preferred embodiment of the method the amino acids are added in concentrations such that the total concentration of stabilizing and viscosity modulating amino acids in the resulting liquid composition is in the range from 150 to 350 mM. Preferably, the total concentration of stabilizing acid(s) and viscosity modulating amino acid(s) are added in concentrations such that in the resulting liquid composition the total concentration is in the range from 200 to 300 mM, more preferably in the range from 225 to 275 mM, most preferably about 250 mM.

According to one embodiment of the method the stabilizing amino acid is glycine and the viscosity modulating amino acid is arginine or a histidine. According to an alternative embodiment of the method the stabilizing amino acid is proline and the viscosity modulating amino acid is arginine or histidine. According to a further alternative embodiment of the method the stabilizing amino acid is glycine or proline and the viscosity modulating amino acids are arginine and histidine. According to a further alternative embodiment of the method the stabilizing amino acids are glycine and proline and the viscosity modulating amino acid is arginine or histidine. According to a further embodiment of the method the stabilizing amino acids are glycine and proline and the viscosity modulating amino acids are arginine and histidine. According to a preferred embodiment of the method, the stabilizing amino acid is glycine and the viscosity modulating amino acid is arginine.

The method according to the third aspect may include the addition of any of the ingredients listed for the liquid composition according to the first aspect. Accordingly, further ingredients described for the liquid composition of the first aspect, in particular the excipients such as detergent, surfactant and sugars may be added before, after or together with the stabilizing and viscosity modulating amino acids. Also, the ingredients may be added before or after the adjustment of the pH. According to one embodiment the excipients are added after addition of the viscosity modulating and stabilizing and amino acids and after the adjustment of the pH.

The method of formulation according to the fourth aspect in particular results in the formation of the liquid composition according to the first aspect.

In a fourth aspect, the present invention further relates to the use of a stabilizing amino acid, in particular the glycine or proline, in combination with a viscosity modulating amino acid, in particular histidine or arginine in the formulation of a highly concentrated polyclonal immunoglobulin preparation. The use of the stabilizing amino acid and modulating amino acid leads to the formation of a liquid composition comprising polyclonal amino acids. In particular, the use leads to the formation of the liquid composition according to the first aspect. The skilled person will understand that the use may contain any of the method steps described for the method according to the third aspect.

The invention is further described by the following non-limiting examples.

EXAMPLES

Example 1—pH Dependence of Immunoglobulin Stability

Immunoglobulin G (IgG) was prepared essentially according to the method as described in WO 2005/082937 A2. Accordingly, the starting material was reconstituted Fraction I+II+III, prepared from a plasma pool, and processed using caprylate precipitation and anion-exchange chromatographies. Dedicated pathogen safety steps comprised solvent/detergent (S/D) treatment, subsequent S/D reagent removal as well as nanofiltration.

Thereafter, the obtained IgG containing solution was concentrated by ultra-/diafiltration and formulated with different buffers. Different compositions were prepared with pH values of 4.5, 5.0, 5.5, 5.9, and 6.2, respectively containing 20 mM NaCl and 20 mM sodium acetate.

The compositions were measured with differential scanning calorimetry (DSC). A MicroCal™ VP-Capillary DSC System was used for the generation of a melting curve as well as determination of midpoint ($T_m$) and enthalpy change of protein unfolding due to heating from 25° C. to 120° C. at a rate of 1° C./min. As calorimetric reference a buffer was used, having the same pH and consisting of the same components as the protein sample, except for the protein.

The results of the measurements are shown in FIG. 1. The thermal transition curves represent the molar heat capacity of the composition in dependence of the temperature and are determined by DSC measurements. The local maxima of the curves represent unfolding transitions. The exact temperatures of the first maximum ($T_m 1$) are identified for each curve. The $T_m 1$-temperatures for said immunoglobulin compositions were 61.3° C. for pH=4.5, 66.2° C. for pH=5.0, 69.2° C. for pH=5.5, 70.6 for pH=5.9 and 71.0° C. at pH=6.2.

With decreasing pH a shift of the thermal transition curve to lower temperatures can be seen in FIG. 1. This means measured protein, in particular immunoglobulins in the composition, melt at lower temperatures with decreasing pH. A decrease of conformational stability of human plasma derived immunoglobulin at lower pH values can be derived from this figure.

In particular at the pH of 4.5, significantly lower thermodynamic immunoglobulin stability can be deduced from the presented data, while higher structural stability can be found at pH values of 5.5 and above.

Example 2—pH Dependence of Immunoglobulin Aggregation

In order to determine the level of aggregation of the immunoglobulin, containing compositions according to example 1 size exclusion chromatography (SEC) was performed using a hydrophilic silica gel suitable for fractionation of globular proteins with relative molecular masses of 10000 to 500000 and detection with a spectrophotometer at 280 nm. The area under the curves of the SEC chromatogram relating to aggregates, dimers, monomers and fragments are calculated. In FIG. 2 the percentage of polymers determined by molecular size distribution in the compositions is presented in relation to the pH.

Example 3—Amino Acid Influence on Immunoglobulin Stability

In this experiment the influence of different amino acids on the immunoglobulin stability was tested using DSC. For this, immunoglobulin compositions were prepared as described in example 1. The finally formulated compositions contain 20 mM NaCl, 20 mM sodium acetate and 230 mM of an amino acid selected from arginine, glycine, proline and histidine adjusted to 5.7. As described in example 1 the thermal transition curves of the four immunoglobulin compositions where determined by DSC. The results are depicted in FIG. 3.

Figure 3:
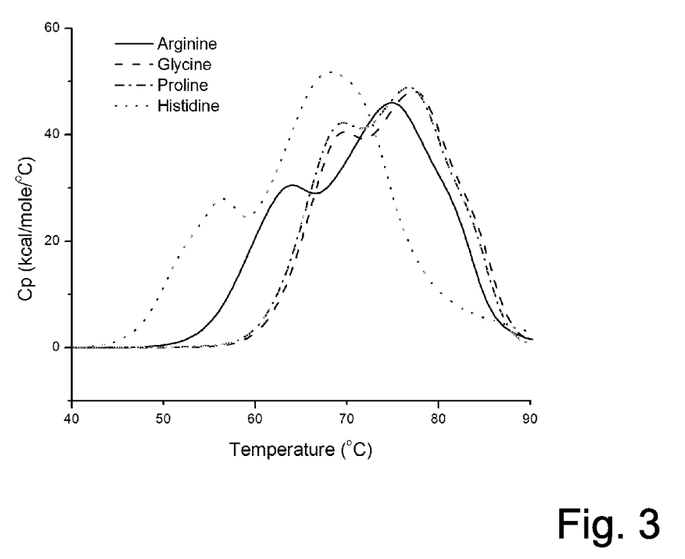
FIG. 3 shows thermal transition curves of compositions comprising human plasma-derived IgG. The thermal transition curves represent the molar heat capacity of the composition in dependence of the temperature and are determined by DSC measurements. The compositions comprise IgG, 20 mM NaCl, 20 mM sodium acetate and have a pH of 5.7. The compositions further comprise either one of arginine, glycine, proline or histidine as indicated in the figure at a concentration of 230 mM. The local maxima of the curves represent unfolding transitions.

Accordingly, from FIG. 3 it is evident that the addition of either glycine or proline leads to the shift of the curve to higher temperatures as compared curves of the compositions containing histidine or arginine. Thus, both glycine and proline can be regarded as stabilizing amino acids.

Example 4—Influence of Amino Acids on Composition Viscosity

In the next step was tested which amino acids are suitable for reducing the viscosity of the immunoglobulin composition. Accordingly, immunoglobulin compositions where prepared as described in example 1 and formulated with 20 mM sodium acetate and 20 mM NaCl at a pH of 5.7. Different amino acid compositions were prepared containing glycine alone or with increasing molar fractions of arginine or histidine with a total amino acid concentration of 250 mM.

The dynamic viscosity of these immunoglobulin compositions was determined with the with the Automated Microviscometer "AMVn" from Anton Paar® GmbH (Austria) at a temperature of +20.0° C. and a capillary inclination angle of 50°.

Figure 4:
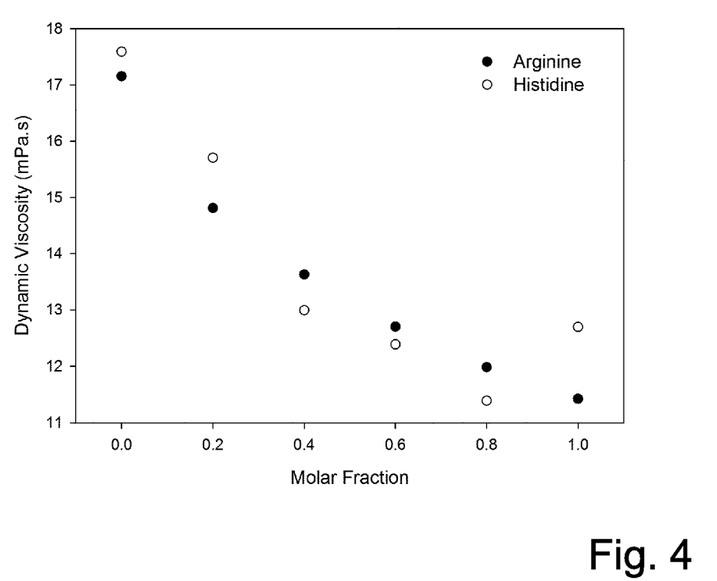
FIG. 4 shows the influence of the concentration of different amino acids on the dynamic viscosity of a composition comprising human plasma-derived IgG. To a composition comprising 20 mM NaCl and 20 mM sodium acetate with a pH of 5.7, amino acids are added to a final concentration of 250 mM and the resulting dynamic viscosity (Y-axis) is determined. The resulting compositions contain glycine and different molar fractions (indicated on the X-axis) of either histidine or arginine. With increasing concentration of arginine or histidine the dynamic viscosity is significantly reduced.

The results are shown in FIG. 4. Accordingly both, arginine and histidine, lead to a strong decrease in dynamic viscosity with increasing molar fractions of said amino acids.

Example 5—Stability of Immunoglobulin Composition with Different Amino Acids

Figure 5:
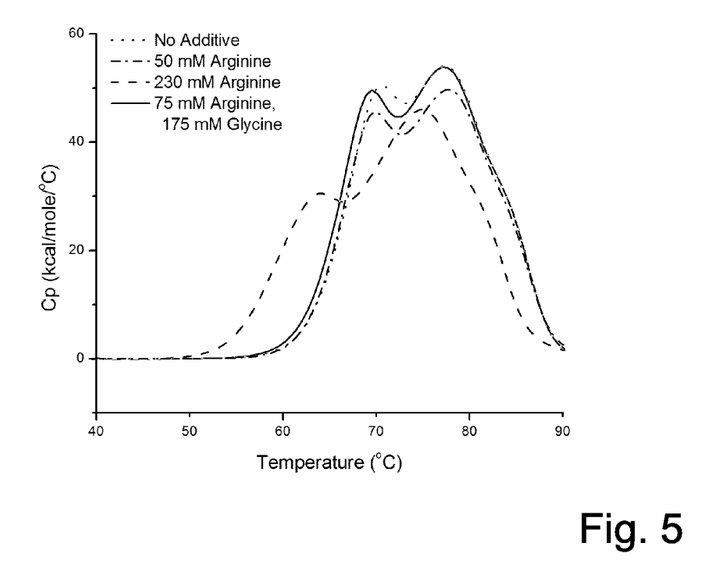
FIG. 5 shows thermal transition curves of compositions comprising human plasma-derived IgG. The thermal transition curves represent the molar heat capacity of the composition in dependence of the temperature and are determined by DSC measurements. The compositions comprise IgG, 20 mM NaCl, 20 mM sodium acetate and have a pH of 5.7. In addition the measured compositions contain either 50 mM arginine, 230 mM arginine, or a mixture of 75 mM arginine and 175 mM glycine or no amino acid ("No Additive") as indicated in the figure.

In the next step a combination of arginine and glycine was attested regarding its effect on the stability of the immunoglobulins in the preparation. An immunoglobulin composition was prepared according to example 1 and formulated with 20 mM sodium acetate and 20 mM NaCl at pH of 5.7. To the first immunoglobulin composition 175 mM glycine and 75 mM arginine were added. As comparison, three compositions were prepared with 50 mM arginine, 230 mM arginine or no additives. Again, the thermal transition curves of the immunoglobulin compositions where measured by DSC. The results are shown in FIG. 5. Accordingly, the composition with 75 mM arginine and 175 mM glycine has a comparable transition to curve to the composition with no additive. In contrast, the use of low amounts of arginine (50 mM) or high amounts of arginine (230 mM) destabilize the composition. The latter result was expected because the decrease of viscosity of the solution often relates to the destabilization of the proteins in the solution.

This experiment shows that the destabilizing effect of the viscosity reduction caused by the viscosity modulating amino acid arginine is completely abolished by use of a sufficient amount of glycine.

Example 6—Viscosity of the Immunoglobulin Composition with Glycine and Arginine

Figure 6:
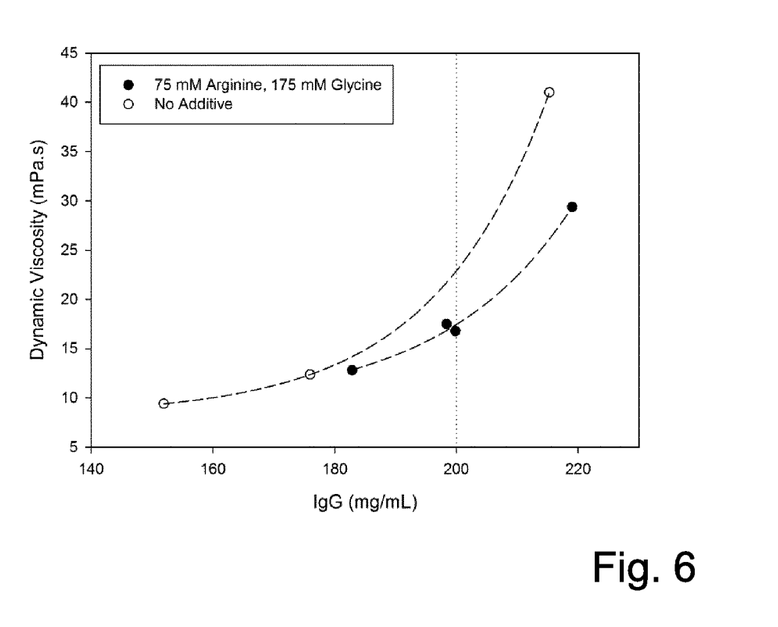
FIG. 6 shows the correlation of IgG concentration and the dynamic viscosity of IgG compositions with and without amino acid additives. Using a combination of arginine and glycine it is possible to reduce viscosity in highly concentrated human plasma-derived IgG solutions with respect to the native, not amino acid stabilised, formulation The curves represent IgG compositions with 20 mM NaCl, 20 mM sodium acetate a pH 5.7 a varying IgG concentrations. The compositions represented by black dots contain 75 mM arginine and 175 mM glycine, the compositions represented by circles do not contain additive ("No additive").

In order to determine whether the stabilizing amino acid glycine has a negative impact on the viscosity of the immunoglobulin composition, the dynamic viscosity of immunoglobulin compositions with 175 mM glycine and 75 mM arginine and increasing concentrations off immunoglobulin (180 g/L, 200 g/L and 220 g/L) were tested as described in example 3. As a comparison also the dynamic viscosity of composition with no additives and increasing amounts of immunoglobulin were measured. The results are shown in FIG. 6. It is evident from the diagram of FIG. 6 that the stabilizing amino acid glycine has no negative impact on the reduction of the viscosity.

Example 7—Storage Stability of Various Immunoglobulin Formulations

Polyclonal immunoglobulin concentrates where prepared as described in example 1. In the following storage experiments different immunoglobulin concentrates where formulated and stored. Before and after storage the composition of the immunoglobulin compositions was tested.

Storage Experiments with Immunoglobulin Formulation 1

The immunoglobulin concentrate was formulated with 20 mM sodium acetate, 20 mM NaCl, 202 mM glycine and 51 mM arginine to an immunoglobulin concentration of 208 g/l at a pH of 5.8. The dynamic viscosity was determined as 20.0 mPa*s. Samples of the immunoglobulin composition were stored at either 2-8° C. or 23-27° C. for 12 months.

The fractions of polymers, dimers, monomers, monomers plus dimers and fragments were determined from chromatograms obtained by size exclusion chromatography before and after storage.

The results of the storages at different temperatures are shown in tables 1 and 2.

TABLE 1

Results from the storage at a temperature of 2-8° C.

| Formulation 1.1 | Initial | 12 months |
|---|---|---|
| Polymers | 0.6 | 1.8 |
| Dimers % | 10.1 | 14.6 |
| Monomers % | 89.3 | 83.7 |
| Mono + Dimers % | 99.4 | 98.3 |
| Fragments % | <0.2 | <0.2 |

TABLE 2

Results from the storage at a temperature of 23-27° C.

| Formulation 1.2 | Initial | 12 months |
|---|---|---|
| Polymers | 0.6 | 0.6 |
| Dimers % | 10.1 | 12.4 |
| Monomers % | 89.3 | 85.2 |
| Mono + Dimers % | 99.4 | 97.6 |
| Fragments % | <0.2 | 1.9 |

Storage Experiments with Immunoglobulin Formulation 2

The immunoglobulin concentrate was formulated with 20 mM sodium acetate, 20 mM NaCl, 173 mM glycine and 74 mM arginine to an immunoglobulin concentration of 207 g/L at a pH of 5.8. The dynamic viscosity was determined as 19.1 mPa*s. Samples of the immunoglobulin composition were stored at either 2-8° C. for 12 months or 23-27° C. for 69 months.

The fractions of polymers, dimers, monomers, monomers plus dimers and fragments were determined from chromatograms obtained by size exclusion chromatography before storage, after 12 months and in case of composition 2.2 after 69 months storage.

The results of the storages at different temperatures are shown in tables 3 and 4.

TABLE 3

Results from the storage at a temperature of 2-8° C.

| Formulation 2.1 | Initial | 12 months | 69 months |
|---|---|---|---|
| Polymers | 0.6 | 1.7 | 2.1 |
| Dimers % | 9.5 | 14.5 | 16.0 |
| Monomers % | 89.9 | 83.8 | 81.3 |
| Mono + Dimers % | 99.4 | 98.3 | 97.3 |
| Fragments % | <0.2 | <0.2 | 0.6 |

TABLE 4

Results from the storage of formulation 2 at a temperature of 23-27° C.

| Formulation 2.2 | Initial | 12 months |
|---|---|---|
| Polymers | 0.6 | 0.4 |
| Dimers % | 9.4 | 12.2 |
| Monomers % | 89.9 | 85.4 |
| Mono + Dimers % | 99.3 | 97.6 |
| Fragments % | <0.2 | 2.0 |

Storage Experiment with Immunoglobulin Formulation 3

The immunoglobulin concentrate was formulated with 20 mM sodium acetate, 20 mM NaCl, 168 mM glycine and 87 mM arginine to an immunoglobulin concentration of 195 g/L at a pH of 5.7. The dynamic viscosity was determined as 19.1 mPa*s. Samples of formulation 3 were stored at 2-8° C. for 67 months.

The fractions of polymers, dimers, monomers, monomers plus dimers and fragments were determined from chromatograms obtained by size exclusion chromatography before storage, after 12 months, after 24 months and after 69 months of storage.

The results of the storages at different temperatures are shown in table 5.

TABLE 5

Results from the storage of formulation 3 at a temperature of 2-8° C.

| Formulation 3 | Initial | 12 months | 24 months | 67 months |
|---|---|---|---|---|
| Polymers | 0.3 | 0.6 | 0.5 | 0.6 |
| Dimers % | 9.3 | 19.8 | 20.2 | 20.3 |
| Monomers % | 90.4 | 79.6 | 79.3 | 78.5 |
| Mono + Dimers % | 99.7 | 99.4 | 99.5 | 98.8 |
| Fragments % | <0.2 | <0.2 | <0.2 | 0.6 |

Storage Experiment with Immunoglobulin Formulation 4

The immunoglobulin concentrate was formulated with 20 mM sodium acetate, 20 mM NaCl, 172 mM glycine and 70 mM arginine to an immunoglobulin concentration of 200 g/L at a pH of 5.7. The dynamic viscosity was determined as 19.1 mPa*s. Samples of formulation 4 were stored at 2-8° C. for 24 months.

The fractions of polymers, dimers, monomers, monomers plus dimers and fragments were determined from chromatograms obtained by size exclusion chromatography before storage, after 12 months, and after 24 months of storage.

The results of the storages at different temperatures are shown in table 6.

TABLE 6

Results from the storage of formulation 4 at a temperature of 2-8° C.

| Formulation 4 | Initial | 12 months | 24 months |
|---|---|---|---|
| Polymers | 0.4 | 0.7 | 0.6 |
| Dimers % | 10.1 | 20.5 | 20.0 |
| Monomers % | 89.5 | 78.8 | 79.4 |
| Mono + Dimers % | 99.6 | 99.3 | 99.4 |
| Fragments % | <0.2 | <0.2 | <0.2 |

Storage Experiment with Immunoglobulin Formulation 5

The immunoglobulin concentrate was formulated with 20 mM sodium acetate, 20 mM NaCl, 172 mM glycine and 77 mM arginine to an immunoglobulin concentration of 200 g/L at a pH of 5.7. The dynamic viscosity was determined as 19.1 mPa*s. Samples of formulation 5 were stored at 2-8° C. for 12 months.

The fractions of polymers, dimers, monomers, monomers plus dimers and fragments were determined from chromatograms obtained by size exclusion chromatography before storage, and after 12 months of storage.

The results of the storages at different temperatures are shown in table 7.

TABLE 7

Results from the storage of formulation 5 at a temperature of 2-8° C.

| Formulation 5 | Initial | 12 months |
|---|---|---|
| Polymers | 0.3 | 0.6 |
| Dimers % | 9.8 | 19.7 |
| Monomers % | 89.9 | 79.6 |
| Mono + Dimers % | 99.7 | 99.4 |
| Fragments % | <0.2 | <0.2 |

Storage Experiments with Immunoglobulin Formulation 6

The immunoglobulin concentrate was formulated with 20 mM sodium acetate, 20 mM NaCl, 150 mM glycine and 100 mM arginine to an immunoglobulin concentration of 210 g/L at a pH of 5.7. The dynamic viscosity was determined as 18.1 mPa*s. Samples of formulation 6 were stored at 2-8° C. or 23-27° C. for 12 months.

The fractions of polymers, dimers, monomers, monomers plus dimers and fragments were determined from chromatograms obtained by size exclusion chromatography before storage, and after 12 months of storage.

The results of the storages at different temperatures are shown in tables 8 and 9.

TABLE 8

Results from the storage of formulation 6 at a temperature of 2-8° C.

| Formulation 6.1 | Initial | 12 months |
|---|---|---|
| Polymers | 0.6 | 1.4 |
| Dimers % | 10.1 | 13.9 |
| Monomers % | 89.3 | 84.7 |
| Mono + Dimers % | 99.4 | 98.6 |
| Fragments % | <0.2 | <0.2 |

TABLE 9

Results from the storage of formulation 6 at a temperature of 23-27° C.

| Formulation 6.2 | Initial | 12 months |
|---|---|---|
| Polymers | 0.6 | 0.4 |
| Dimers % | 10.1 | 11.2 |
| Monomers % | 89.3 | 86.2 |
| Mono + Dimers % | 99.4 | 97.4 |
| Fragments % | <0.2 | 2.1 |

Storage Experiments with Immunoglobulin Formulation 7

The immunoglobulin concentrate was formulated with 20 mM sodium acetate, 20 mM NaCl, 196 mM glycine and 51 mM arginine to an immunoglobulin concentration of 184 g/L at a pH of 5.7. The dynamic viscosity was determined as 12.2 mPa*s. Samples of formulation 7 were stored at 2-8° C. or 23-27° C. for 12 months.

The fractions of polymers, dimers, monomers, monomers plus dimers and fragments were determined from chromatograms obtained by size exclusion chromatography before storage, and after 12 months of storage.

The results of the storages at different temperatures are shown in tables 10 and 11.

TABLE 10

Results from the storage of formulation 7 at a temperature of 2-8° C.

| Formulation 7.1 | Initial | 12 months |
|---|---|---|
| Polymers | 0.6 | 1.7 |
| Dimers % | 7.2 | 14.9 |
| Monomers % | 92.2 | 83.4 |
| Mono + Dimers % | 99.4 | 98.3 |
| Fragments % | <0.2 | <0.2 |

TABLE 11

Results from the storage of formulation 7 at a temperature of 23-27° C.

| Formulation 7.2 | Initial | 12 months |
|---|---|---|
| Polymers | 0.6 | 0.6 |
| Dimers % | 7.2 | 12.4 |
| Monomers % | 92.2 | 85.2 |
| Mono + Dimers % | 99.4 | 97.7 |
| Fragments % | <0.2 | 1.9 |

REFERENCES

Bolli R, Woodtli K, Bärtschi M, Hofferer L, Lerch P. L-Proline reduces IgG dimer content and enhances the stability of intravenous immunoglobulin (IVIG) solutions; Biologicals. 2010; 38(1):150-157.

Chi E Y, Krishnan S, Randolph T W, Carpenter J F. Physical stability of proteins in aqueous solution: Mechanism and driving forces in nonnative protein aggregation. Pharm Res. Springer; 2003; 20(9):1325-36.

McCue J P, Hein R H, Tenold R. Three generations of immunoglobulin G preparations for clinical use; Rev Infect Dis. 1986; 8 Suppl 4:S374-81.

Mueller M, Loh M Q T, Tee D H Y, Yang Y, Jungbauer A. Liquid formulations for long-term storage of monoclonal IgGs; Appl Biochem Biotechnol. 2013; 169:1431-48.

Szenczi Á, Kardos J, Medgyesi G a., Závodszky P—The effect of solvent environment on the conformation and stability of human polyclonal IgG in solution. Biologicals. 2006; 34:5-14.

Trevino S R, Scholtz J M, Pace C N. Measuring and Increasing Protein Solubility; 2008; 97(10):4155-66

Wang W, Roberts C J, editors. Aggregation of Therapeutic Proteins; John Wiley & Sons, Inc., Hoboken, New Jersey; 2013.325-356.

Vermeer A W P, Norde W. The thermal stability of immunoglobulin: unfolding and aggregation of a multi-domain protein; Biophys J; 2000 January; 78(1):394-404.

Wang W, Singh S, Zeng D L, King K, Nema S. Antibody structure, instability, and formulation; J Pharm Sci. 2007; 96(1):1-26.

Weiss I V, William F, Young T M, Roberts C J. Principles, approaches, and challenges for predicting protein aggregation rates and shelf life; J Pharm Sci.; 2009; 98(4): 1246-77.

The invention claimed is:

1. A liquid composition comprising polyclonal immunoglobulins, a viscosity-modulating amino acid, and a stabilizing amino acid,
wherein the viscosity-modulating amino acid is arginine and the stabilizing amino acid is glycine,
wherein the total concentration of the stabilizing amino acid and the viscosity-modulating amino acid is in the range of 200 to 300 mM, wherein the concentration of the stabilizing amino acid is in the range of 80 to 220 mM, and wherein the concentration of the viscosity-modulating amino acid is at least 65 mM, wherein more than 90% of the polyclonal immunoglobulins are in the form of monomers or dimers and less than 5% are in the form of polymers, and wherein the immunoglobulin concentration in the composition is above 160 g/L and the pH is in the range from 5.5 to 5.9.

2. The liquid composition according to claim 1, wherein the immunoglobulin concentration is in the range from above 160 to 300 g/L.

3. The liquid composition according to claim 2, wherein the immunoglobulin concentration is in the range from above 160 to 260 g/L.

4. The liquid composition according to claim 1, wherein the pH is in the range from 5.6 to 5.8.

5. The liquid composition according to claim 1, characterized by an immunoglobulin concentration in the range from above 160 to 180 g/L and a dynamic viscosity in the range from 5 to ≤12 mPa*s.

6. The liquid composition according to claim 1, wherein the preparation has a storage stability of at least 40 months at 2 to 8° C.

7. The liquid composition according to claim 1, wherein the composition contains sodium acetate in the range from 10 to 30 mM and/or sodium chloride in the range from 10 to 30 mM.

8. The liquid composition according to claim 1, wherein the composition contains sodium acetate and sodium chloride at a concentration of about 20 mM.

9. The liquid composition according to claim 1, containing one or more excipients selected from surfactant, detergent, or saccharide.

10. The liquid composition according to claim 1, wherein the concentration of the stabilizing amino acid is in the range from 160 to 190 mM.

11. The liquid composition according to claim 1, wherein the total concentration of the stabilizing amino acid and the viscosity-modulating amino acid is in the range from 225 to 275 mM.

12. The liquid composition according to claim 1, wherein the composition has haemagluttinin titers of ≤16 for anti-A and ≤8 for anti-B as determined by the Direct Coombs Test.

13. A method of treatment that comprises administering the liquid composition according to claim 1 to a patient by intramuscular injection or subcutaneous injection.

14. A of formulating a polyclonal immunoglobulin composition, comprising:

(a) providing a polyclonal immunoglobulin composition with an immunoglobulin concentration of above 160 g/L, (b) adjusting the pH of the composition to a value in the range from 5.5 to 5.9, and (c) adding glycine to the composition as a stabilizing amino acid and adding arginine to the composition as a viscosity-modulating amino acid such that the total concentration of the stabilizing amino acid and the viscosity-modulating amino acid is in the range of 200 to 300 mM, wherein the concentration of the stabilizing amino acid is in the range of 80 to 220 mM, and wherein the concentration of the viscosity-modulating amino acid is at least 65 mM.

15. The liquid composition according to claim 1, characterized by an immunoglobulin concentration in the range from above 180 to 220 g/L and a dynamic viscosity of >12 to ≤35 mPa*s.

16. The liquid composition according to claim 1, characterized by an immunoglobulin concentration in the range from above 220 to 260 g/L and a dynamic viscosity of >35 to ≤100 mPa*s.

* * * * *